United States Patent [19]

Vitale

[11] Patent Number: 5,984,960
[45] Date of Patent: Nov. 16, 1999

[54] ROTARY TORQUE TO AXIAL FORCE ENERGY CONVERSION APPARATUS

[75] Inventor: Nicholas Gerard Vitale, Albany, N.Y.

[73] Assignee: Mechanical Technology Inc., Latham, N.Y.

[21] Appl. No.: 08/885,142

[22] Filed: Jul. 1, 1997

Related U.S. Application Data

[62] Division of application No. 08/640,172, Apr. 30, 1996, abandoned.

[51] Int. Cl.$^6$ ........................................................ A61F 2/22
[52] U.S. Cl. .................................. 623/3; 600/16; 417/418
[58] Field of Search ........................... 600/16–17; 623/3; 417/417, 418; 415/900

[56] References Cited

U.S. PATENT DOCUMENTS

| | | | |
|---|---|---|---|
| 3,483,412 | 12/1969 | Bakker et al. | 310/12 |
| 3,716,731 | 2/1973 | Nilsson | 310/13 |
| 4,652,265 | 3/1987 | McDougall | 623/3 |
| 4,718,903 | 1/1988 | Min et al. | 623/3 |
| 4,754,181 | 6/1988 | Mizobuchi et al. | 310/104 |
| 4,822,357 | 4/1989 | Forster et al. | 623/3 |
| 5,079,458 | 1/1992 | Schuster | 310/12 |
| 5,263,979 | 11/1993 | Isoyama et al. | 623/3 |
| 5,300,111 | 4/1994 | Panton et al. | 623/3 |
| 5,314,469 | 5/1994 | Gao | 623/3 |
| 5,360,445 | 11/1994 | Goldowsky | 623/3 |
| 5,728,154 | 3/1998 | Crossett et al. | 623/3 |
| 5,762,599 | 6/1998 | Sohn | 60/30 |

OTHER PUBLICATIONS

Korane, Kenneth J., "Replacing the Human Heart", Machine Design, pp. 100–105, Nov. 1991.

Massiello et al., "The Cleveland Clinic–Nimbus Total Artificial Heart, Design and in Vitro Function," Journal of Thoracic and Cardiovascular Surgery, vol. 108, No. 3, pp. 412–419, Sep. 1994.

McCarthy et al., "The Cleveland Clinic–Nimbus Total Artificial Heart, In Vivo Hemodynamic Performance in Calves and Preclinical Studies," Journal of Thoracic and Cardiovascular Surgery, vol. 108, No. 3, pp. 420–428, Sep. 1994.

Rintoul et al., "Continuing Development of the Cleveland Clinic–Nimbus Total Artificial Heart", ASAIO Journal, pp. M168–M171, 1993.

Harasaki et al., "Progress in Cleveland Clinic–Nimbus Total Artificial Heart Development", ASAIO Journal, pp. M494–M498, 1994.

Hogness et al., "The Artificial Heart, Prototypes, Policies, and Patients," Institute of Medicine, National Academy Press, pp. 1–125, 1991.

Rosenberg et al., "A Roller Screw Drive For Implantable Blood Pumps," Trans. Am Socl. Artif. Intern. Organs, vol. XXVIII, pp. 123–125, 1982.

*Primary Examiner*—Bruce E. Snow
*Attorney, Agent, or Firm*—Heslin & Rothenberg, P.C.

[57] ABSTRACT

A rotary torque-to-axial force energy conversion apparatus employs a rotatable member, a translatable member, and a magnetic coupling therebetween. The magnetic coupling converts a rotary torque on the rotatable member to an axial force on the translatable member, and includes a first permanent magnet comprising part of the rotatable member and a second permanent magnet comprising part of the translatable member. By way of example, the first permanent magnet and the second permanent magnet may each comprise interleaved, helical magnet sections of alternating polarities. A significant application of the energy conversion apparatus comprises an actuator apparatus for a ventricle assist device (VAD) or a total artificial heart (TAH). By oscillating the drive motor energizing the rotatable member, an oscillating rotary torque is achieved that is converted by the magnetic coupling to a reciprocating axial motion on the translatable member. The reciprocating axial motion is employed within a Cleveland Clinic—type TAH to alternately actuate a first diaphragm coupled to a first ventricle and a second diaphragm coupled to a second ventricle for alternately pumping blood from the ventricles. An axial force-to-rotary torque energy conversion apparatus is also described.

6 Claims, 5 Drawing Sheets

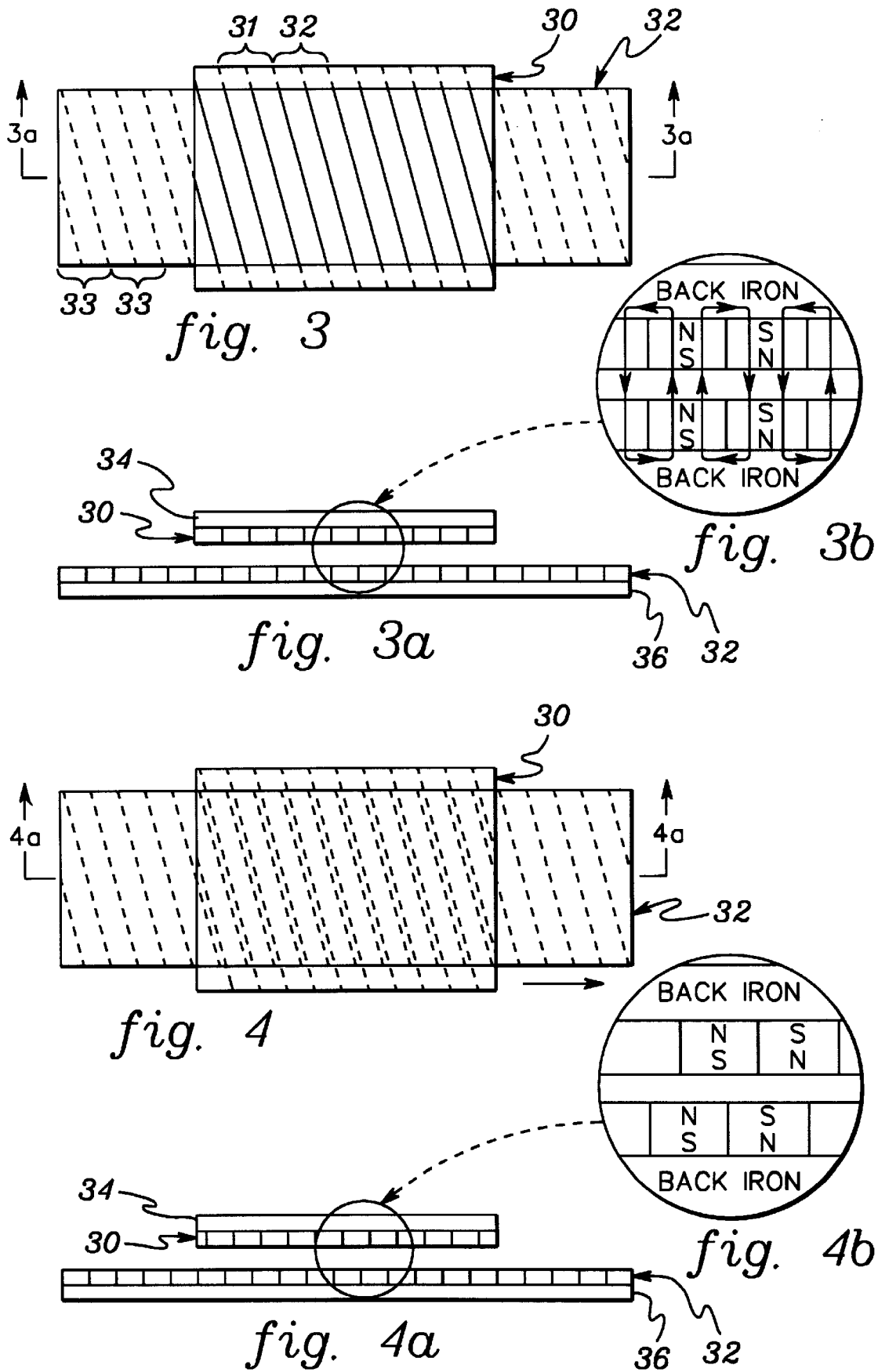

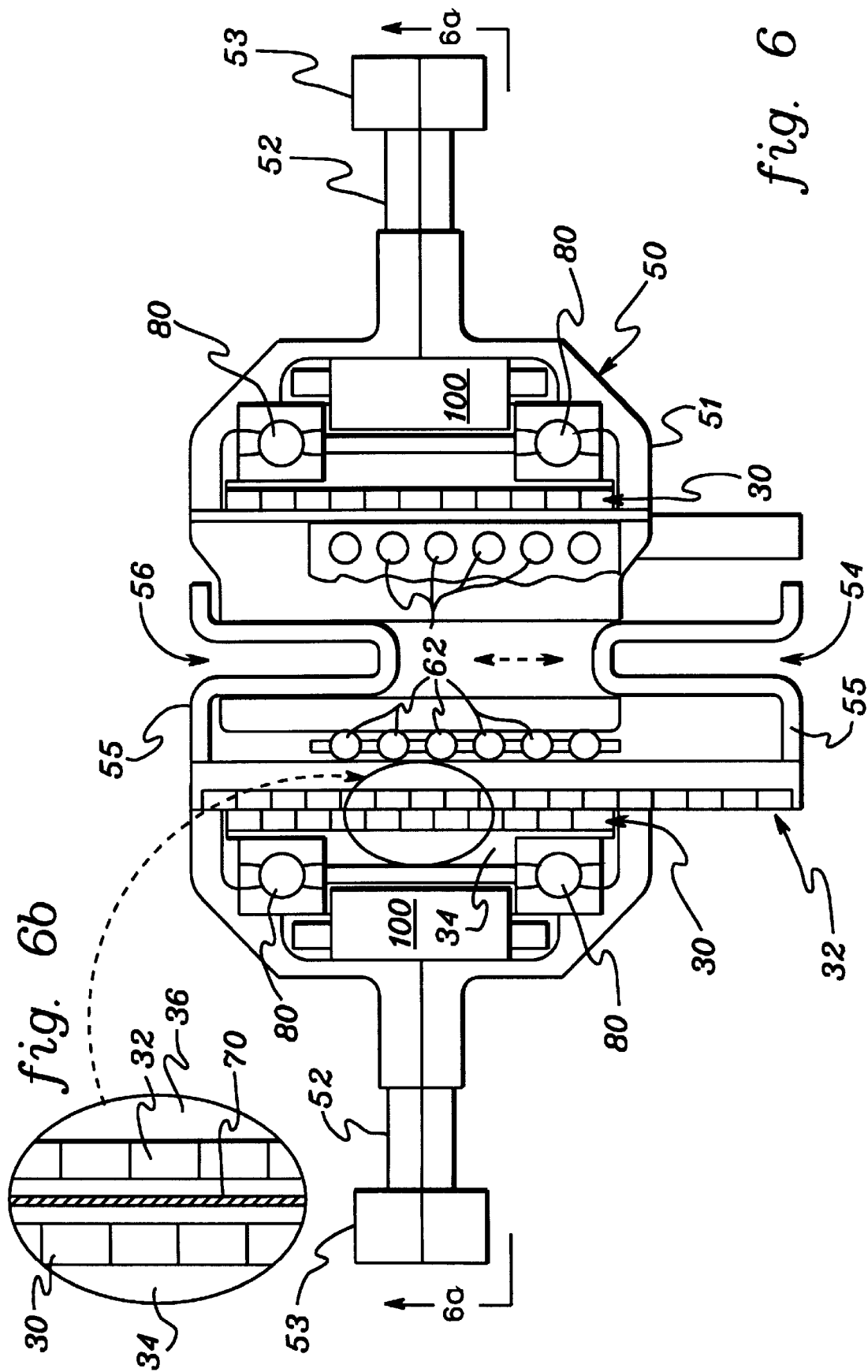

ROTARY TORQUE TO AXIAL FORCE ENERGY CONVERSION APPARATUS

This application is a division of application Ser. No. 08/640,172 filed Apr. 30, 1996 which application is now abandoned.

TECHNICAL FIELD

The present invention relates in general to an energy conversion apparatus employing a magnetic coupling for converting rotary torque to axial force or axial force to rotary torque. A significant application of the energy conversion mechanism is in the field of artificial hearts wherein the mechanism can be employed in an actuator for a ventricle assist device (VAD) or for pumping blood from one or two ventricles of a total artificial heart (TAH).

BACKGROUND ART

Implantable blood pumps or artificial hearts have been the subject of significant work for several decades. Although much progress has been made, no approach has demonstrated the high reliability needed for an actuator. Generally, most existing approaches employ conversion of the motion of a rotary electric motor into the linear motion of a pusher plate to squeeze blood from rubber-type ventricles. Some employ a hydraulic piston to squeeze the ventricles with fluid, while some push on the ventricles directly using no hydraulics. Such rotary-to-linear conversion mechanisms, including lead screws, gear pumps and a host of other designs, are all prone to primary component wear and breakdown. Thus, most, if not all, existing actuator approaches have undesirable reliability concerns associated therewith. In fact, existing actuator approaches comprise a major stumbling block in attaining a highly reliable, light weight prosthesis.

One type of artificial heart is depicted in FIGS. 1, 2a & 2b. This total artificial heart (TAH) 10, provided by the Cleveland Clinic, includes blood inflow ports and valves 12 and blood outflow ports and valves 14. As best shown in FIGS. 2a & 2b, the TAH 10 includes two blood pumps, a right blood pump or ventricle 20 and a left blood pump or ventricle 22 within a housing 18. Each blood pump 20 & 22 includes a reciprocable diaphragm 21 & 23, respectively, which is mechanically coupled to a corresponding pusher plate 21' & 23' powered by an interventricular energy converter or actuator 26. Actuator 26, which pilots a guide pin 25 affixed to pusher plate 21' and a guide pin 27 affixed to pusher plate 23', produces an axial reciprocating motion which, during eject mode, drives one pusher plate 21' or 23' towards the TAH 10 housing 18.

The heart is controlled by responding to venous pressure, because more flow is required as pressure increases. The follower is not directly coupled to either pusher plate. Thus, while blood from one blood pump is being ejected, the other is free to fill, with the rate of filling depending on venous return pressure. During fill, each guide pin is free to slide within the actuator, so diaphragm fill cycle motion is determined by venous pressure, rather than the actuator rate. Control logic senses the velocity or position of the diaphragm, and maintains an actuator speed sufficient to avoid fill cycle contact between pusher plate and actuator, without running so fast that efficiency or operation of the opposite pump is impacted. A ventricular assist device operates similarly, except that only one pump is involved.

The TAH 10 can be equivalently operated by a number of different, existing interventricular actuators. For example, most existing electromechanical actuators could be employed. The Cleveland Clinic—type TAH conventionally employs an electrohydraulic energy conversion apparatus. This apparatus comprises a brushless DC motor which turns a gear pump that provides hydraulic flow at about 100 psi. Internal valving controls flow to a double-ended hydraulic actuator. To ensure that the system is hermetically sealed, the actuator piston is actually a stack of magnets riding in the cylinder, with a follower magnet outside the cylinder to match piston motion. The follower magnets are attached to a translating element that presses against a pusher plate that deflects the rubber diaphragm. For further information on this actuator, reference: Massiello et al., "The Cleveland Clinic—Nimbus Total Artificial Heart," Journal of Thoracic and Cardiovascular Surgery, Vol. 108, No. 3, pp. 412–419 (1994); and Harasaki et al., "Progress in Cleveland Clinic—Nimbus Total Artificial Heart Development," ASAIO Journal, M494–M498 (1994).

Although existing energy conversion approaches have been successful to varying extents, the art would be advanced by a next-generation actuator for permanently implantable pulsatile ventricle assist devices and/or total artificial hearts which eliminates mechanical contact and wear between the principal rotary-to-linear motion conversion elements. The present invention provides this advancement.

DISCLOSURE OF INVENTION

Briefly summarized, the invention comprises in a first aspect a rotary torque-to-axial force energy conversion apparatus which includes a rotatable member and a translatable member. A magnetic coupling is provided between the rotatable member and the translatable member for converting rotary torque of the rotatable member to an axial force on the translatable member. The magnetic coupling may comprise permanent magnets including a first permanent magnet comprising part of the rotatable member and a second permanent magnet comprising part of the translatable member.

In one embodiment, the first permanent magnet comprises interleaved, helical magnet sections of alternating polarities, as does the second permanent magnet. These helical structures have the same pitch. The translatable member resides at least partially within the rotatable member, and the apparatus includes a mechanism for preventing rotation of the translatable member such that rotary torque of the first permanent magnet is converted to axial movement of the second permanent magnet, and hence the translatable member. The apparatus for imparting rotary torque to the rotatable member can comprise a permanent magnet rotary motor which imparts oscillating motion to the rotatable member, thereby producing an oscillating rotary torque at the first permanent magnet that in turn produces reciprocating axial movement in the second permanent magnet, and hence the translatable member.

In a further aspect, the invention comprises an axial force-to-rotary torque energy conversion apparatus. This apparatus also includes a translatable member and a rotatable member. A magnetic coupling is provided between the translatable member and the rotatable member for converting an axial force on the translatable member into a rotary torque on the rotatable member. The magnetic coupling can comprise a first permanent magnet associated with the translatable member and a second permanent magnet associated with the rotatable member. Each permanent magnet may be structured as interleaved, helical magnet sections of alternating polarities.

In another aspect, the invention comprises an actuator apparatus for a ventricle assist device (VAD) or a total artificial heart (TAH). The actuator apparatus includes a rotatable member and a translatable member. Drive means are provided for imparting rotary torque to the rotatable member, and a magnetic coupling converts rotary torque on the rotatable member to an axial force on the translatable member; the axial force on the translatable member being employed as a driver for the VAD or TAH. The magnetic coupling resides between the rotatable member and the translatable member.

In still another aspect, the invention consists of a total artificial heart (TAH) comprising a housing having a first ventricle and a second ventricle. A first diaphragm is coupled to the first ventricle for pumping blood therefrom when actuated towards the housing, while a second diaphragm is coupled to the second ventricle for similarly pumping blood therefrom when actuated towards the housing. The TAH also includes an actuator for actuating at least one diaphragm of the first diaphragm and the second diaphragm. The actuator includes a rotatable member and a translatable member, as well as drive means for imparting rotary torque to the rotatable member. A magnetic coupling is associated with the rotatable member and the translatable member for converting rotary torque of the rotatable member to an axial force on the translatable member. The axial force on the translatable member is employed to actuate the at least one diaphragm to pump blood from at least one of the first ventricle and the second ventricle.

Further enhancements of all aspects of the invention are described and claimed in greater detail herein.

To restate, the present invention broadly comprises a rotary torque-to-axial force (or axial force-to-rotary torque) energy conversion apparatus, with one significant application thereof comprising an actuator for a total artificial heart (TAH) or for a ventricle assist device (VAD). An actuator in accordance with this invention employs a magnetic coupling which totally eliminates contact, wear and friction between the principal moving elements of the actuator. The magnetic coupling, which consists of a helically wound pair of radially polarized magnets of opposite polarity, takes place through a thin isolation wall that permits important bearing components and their lubricants to be sealed. These components, along with the drive motor, are therefore also isolated from the humid inter-pump space. The new actuator is expected to provide much longer life, lower heat generation, and increased reliability, compared to existing systems. Combined with a new electric motor which takes advantage of the latest magnet materials and design technology, the actuator will be more compact than present electromechanical actuators, providing an improved anatomical fit.

BRIEF DESCRIPTION OF DRAWINGS

The subject matter which is regarded as the present invention is particularly pointed out and distinctly claimed in the concluding portion of the specification. The invention, however, both as to organization and methods of practice, together with further objects and advantages thereof, may best be understood by reference to the following detailed description taken in conjunction with the accompanying drawings in which:

FIG. 3 is an elevational view of one embodiment of a magnetic coupling between a rotatable member and a translatable member in accordance with the present invention;

FIG. 3a is a partial cross-sectional view of the magnet members of FIG. 3 taken along line 3a—3a;

FIG. 4 comprises an elevational view of the magnet members of FIG. 3 wherein the rotatable member has been displaced, thereby applying a force to the translatable member;

FIG. 4a is a partial cross-sectional view of the magnet members of FIG. 4 taken along line 4a—4a;

FIG. 6 is an elevational view of the rotary torque-to-axial force energy conversion actuator of FIG. 5; and FIG. 6a is a partial cross-sectional view of the actuator of FIG. 6 taken along line 6a—6a.

BEST MODE FOR CARRYING OUT THE INVENTION

Figure 1:
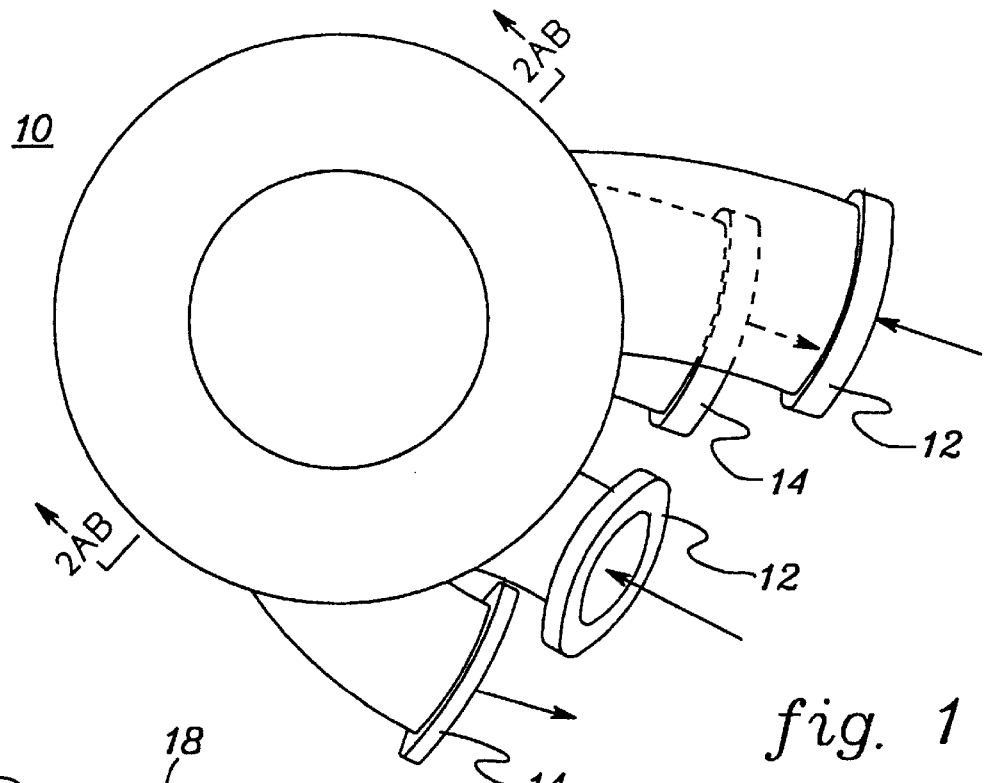
FIG. 1 is an elevational view of a Cleveland Clinic—type total artificial heart (TAH) to employ an actuator in accordance with the present invention.

Conceptually, one preferred embodiment of a rotary torque-to-axial force (or axial force-to-rotary torque) energy conversion coupling in accordance with the present invention is analogous to a mechanical screw coupling wherein the mechanical thread is replaced by a "magnetic thread" having no contact, wear, or friction between the moving elements of the magnetic coupling. One example of this magnetic thread coupling is depicted by way of example in FIGS. 3 & 3a. In the elevational view of FIG. 3, a first magnet member 30 of the magnet coupling is assumed to comprise a cylindrical structure within which a second magnet member 32, also a cylindrical structure, resides. First magnet member 30 comprises interleaved magnet sections, or more definitively, a magnetic thread consisting of a spiral wound pair 31 of radially polarized magnets of opposite polarity. Similarly, second magnetic member 32 comprises a spiral wound pair 33 of radially polarized magnets of opposite polarity.

The outer surfaces of magnet pair 33 (i.e., the surfaces facing magnet member 30) define a smooth cylinder with no interlocking ridges, while the inner surfaces of magnet pair 33 (i.e., the surfaces facing away from mating magnet member 30) are backed by a smooth cylindrical structure 36 (FIG. 3a) made from steel or other flux carrying material, which defines a flux return path. Magnet member 30 has a similar magnet structure and is sized so that the first and second magnet members fit concentrically one inside the other without making physical contact. The inner surface of magnet member 30 comprises the spirally wound pair 31 of radially polarized magnets of opposite polarity, while an outer surface thereof is surrounded by a back iron 34 (FIG. 3a) to return magnetic flux as depicted in the partial enlargement shown in FIG. 3a.

The magnet pairs 31 & 33 of the magnet members 30 & 32, respectively, tend to align themselves such that magnetic fluxes align with each other. An aligned magnetic coupling is depicted in FIGS. 3 & 3a. As best shown in the enlargement of FIG. 3a, polarities alternate as you move down the magnetic coupling. With the two members so aligned, no rotational torque or axial force exists between them. This is the null force position, or the relative position to which the magnet coupling returns when no external forces act on either member.

FIG. 4 depicts the case where magnet members 30 & 32 are displaced relative to one another in the tangential direction, e.g., by rotating member 30, and a relative force is generated between the two members, tending to return them to the null position. In this example, this force includes an axial force on member 32 in the direction shown by the arrow. This axial force component of the magnet coupling will comprise the force an actuator applies to one of the blood pumps. The tangential component of the axial force generates the torque that the rotary drive motor must overcome to activate the magnetic coupling.

As shown in FIGS. 4 & 4a, the magnetic coupling can serve as either a rotary torque-to-axial force energy conversion coupling or an axial force-to-rotary torque energy conversion coupling. Whenever a torque or force is applied to one magnetic member of the coupling, the other magnetic member will respond by attempting to follow the motion of the magnet member to which the torque or force is applied. This can be understood with reference to the enlarged portion of FIG. 4a wherein application, for example, of a rotary torque to first magnetic member 30 results in the shown offset between the two magnet members such that the second magnet member 32 will want to rotate or translate to align with the first magnet member. Thus, by constraining linear motion of first magnet member 30 and rotary motion of second magnet member 32, a rotary torque-to-axial force energy conversion coupling is attained. Conversely, by constraining rotary motion of member 30, and linear motion of member 32, then an axial force-to-rotary torque energy conversion coupling is achieved, wherein it is assumed that energy is applied to magnetic member 30.

Three parameters that impact design of the magnetic coupling are its diameter, pitch and clearance between the facing surfaces of the two magnet members. Selection of the second magnet member diameter is based on a trade-off between the surface area of the second magnet member (and hence maximum force capability) and, in an actuator design, the volume available for the drive motor and linear bearing (discussed further below). Decreasing magnet member diameters increases the volume available for the rotary motor and rotary bearings. Selection of the magnetic member pitch is based on a trade-off between the actuation torque of the rotary motor and the motor rotational speed (and hence the torsional inertial and gyroscopic effects). Increasing the pitch increases the motor actuation torque and hence the motor coil loss, but reduces the maximum motor speed and hence the torsional inertial and gyroscopic effects. Selection of the clearance between the first magnet member and the second magnetic member is based on a trade-off between mechanical design considerations (manufacturing and assembly tolerances) and magnetic coupling force capability. Reducing the clearance between the mating parts increases the force capability of the magnetic coupling, particularly at low values of pitch.

Again, a significant advantage of the magnetic coupling presented herein is a complete elimination of wear and loss of primary actuator elements. Wear and loss do still exist in secondary mechanisms, such as rotary and axial bearings, discussed below. However, these bearings are generally much more lightly loaded than the primary mechanisms and can be consequently designed for a much longer life. Design considerations in employing a magnetic coupling as presented herein include the force generation capability and the relatively low mechanical stiffness between the mating magnetic members. These two considerations imply that the magnetic coupling is particularly well suited for a ventricle assist device (VAD) or total artificial heart (TAH) actuator since a primary requirement thereof is long life and high reliability, and the force requirement is within the capability of the magnetic coupling, while precision positioning is not required. In fact, compliance within the actuator is actually desirable.

Figure 2A:
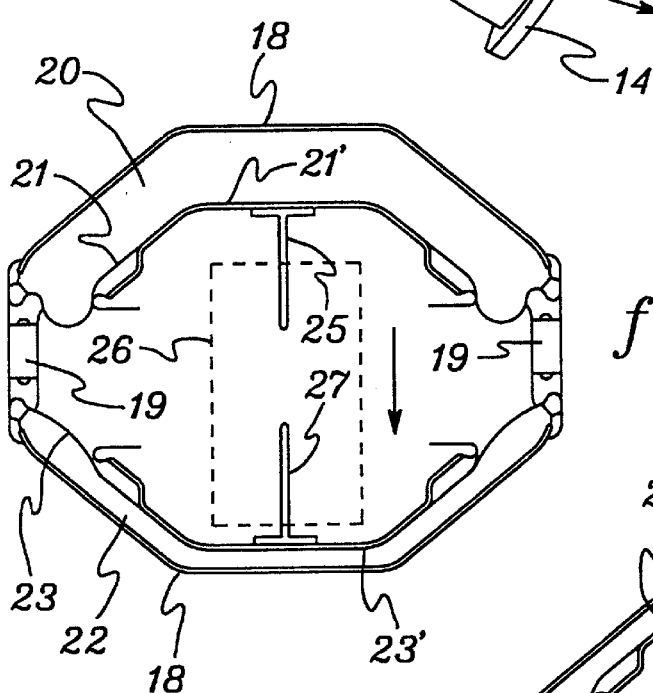
FIGS. 2a & 2b are cross-sectional depictions of the TAH of FIG. 1 taken along line 2AB—2AB, wherein in FIG. 2a the actuator has applied force to a left blood pump, and in FIG. 2b the actuator has applied force to a right blood pump.
Figure 2B:
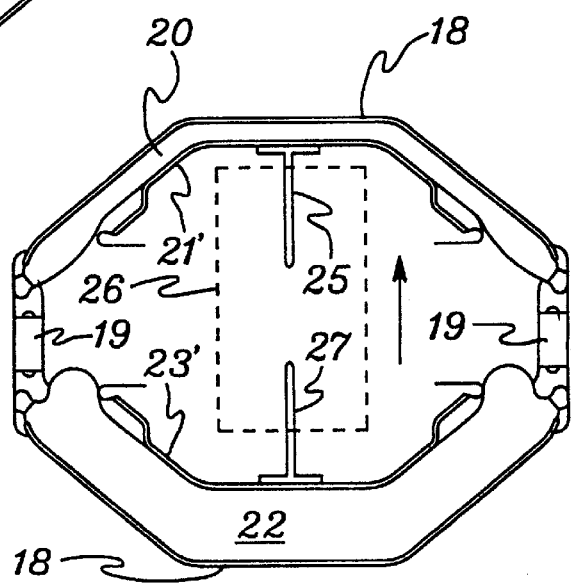
Figure 5:
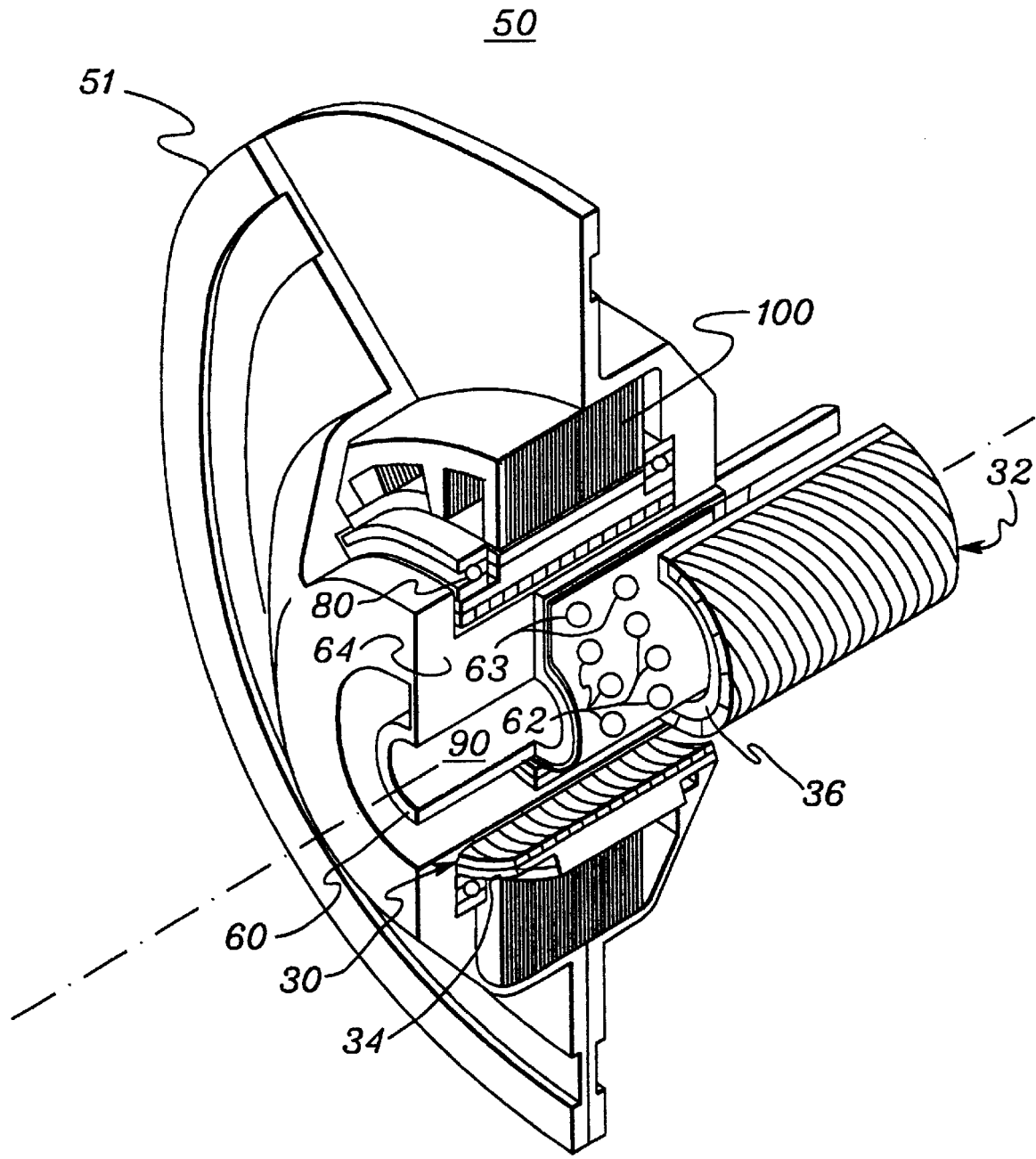
FIG. 5 is a partial cut-away, partially exploded perspective view of a rotary torque-to-axial force energy conversion actuator in accordance with the present invention for a TAH or VAD.
Figure 6A:
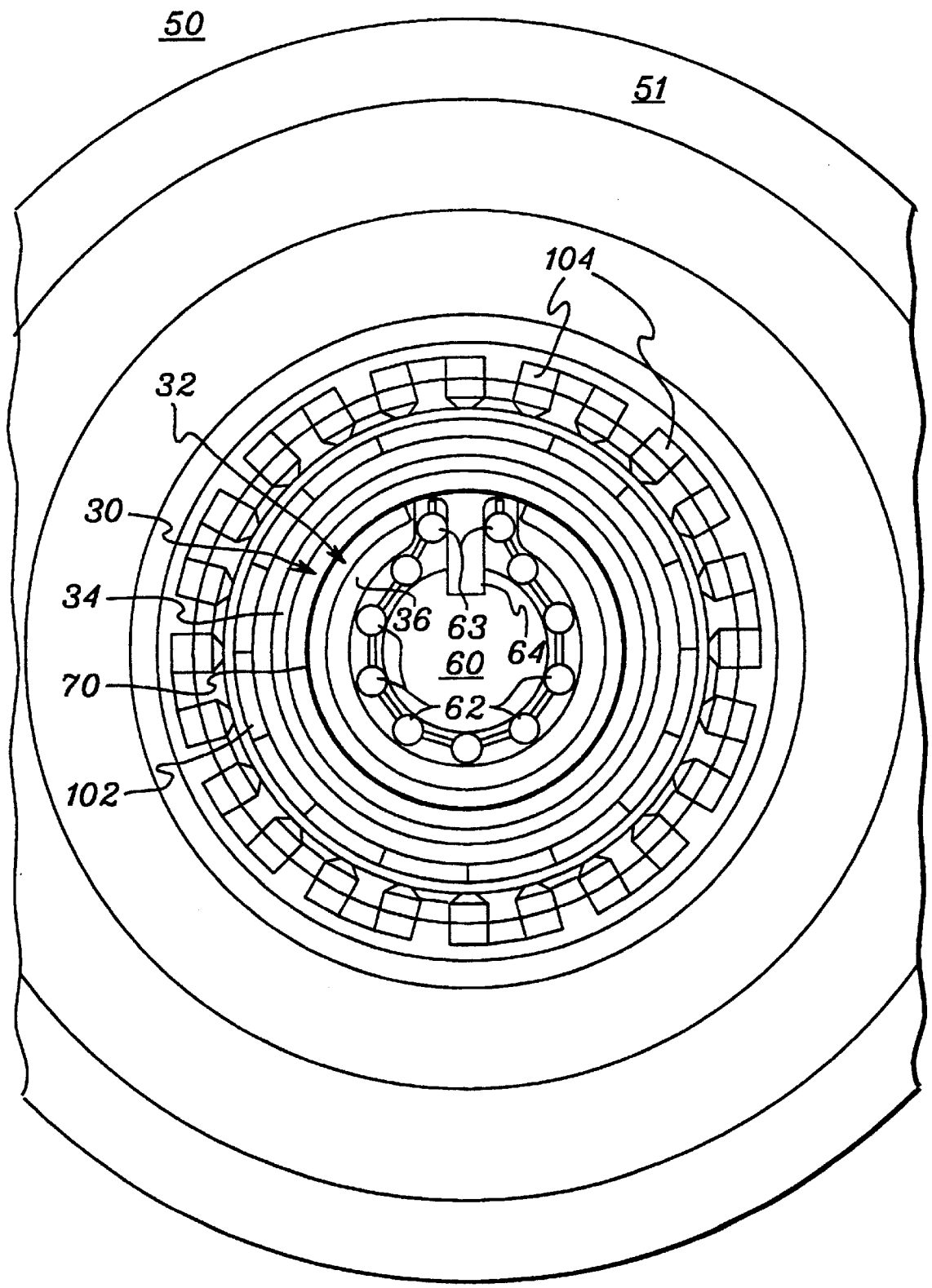

FIGS. 5, 6 & 6a depict use of the magnetic coupling concept within an actuator, generally denoted 50, designed for a Cleveland Clinic—type total artificial heart (TAH) such as shown in FIGS. 1, 2 & 2a. As best shown in FIG. 6, actuator 50 is shaped (and sized) to fit within the Cleveland Clinic—type TAH summarized herein and discussed in greater detail in the initially referenced articles. Actuator 50 is to reside within the interventricular space within the TAH, with channels 52 defined adjacent to flanged ends 53 designed to pertrude through O-rings surrounding openings 19 in the TAH to hold the actuator in place relative to the TAH housing. A plunger 55 is attached to the linearly moving, second magnet member 32 of the magnetic coupling. Plunger 55 includes a first opening 54 and a second opening 56, each of which is sized to accommodate a respective guide pin 27 & 25 coupled to the pusher plates. With orientation of actuator 50 as shown in FIG. 6, the magnetic coupling can be employed to achieve a reciprocating up/down linear motion with plunger 55 alternately pushing against the first pusher plate 21' and the second pusher plate 23' (FIGS. 2a & 2b).

Principal components of actuator 50 include: the rotating and translating magnet members 30 & 32, respectively, of the magnetic coupling; rotary radial and thrust bearings 80 for rotating member 30; axial and anti-rotation bearing apparatus 90 for translating magnet member 32; a brushless permanent magnet drive motor 100 for applying rotary torque to the rotating magnet member 30; an actuator casing 51; and a thin pressure vessel wall 70 between rotating member 30 and translating member 32 which permits hermetic sealing of the rotary drive system. The rotating and translating magnetic members of the magnetic coupling are summarized above, while the remaining components of the actuator are discussed in greater detail below.

Axial and anti-rotation bearing apparatus 90 is a significant component of the actuator design. A principal requirement for bearing 90 is for a long life and high reliability in a non-lubricated, low temperature, high humidity environment. A key to achieving this design requirement is a low bearing load and speed, and proper selection of bearing materials, which can be accomplished by one of ordinary skill in the art. The loads on the axial bearings 62 and anti-rotation bearings 63 may be divided into primary loads and secondary loads. Primary loads are those loads that are determined by the fundamental force generation processes. These loads can be controlled by varying actuator 50 design parameters. An example of a primary load is the torque load on anti-rotation bearings 63 between translating magnet member 32 and immovable arm 64 mechanically coupled to housing 51. Arm 64 connects to a mandrel 60 to allow translation of member 32, while preventing rotation thereof. This is possible since as shown, member 32 is elongate with a C-shape traverse cross-section and arm 64 depends through the opening in the C-shape cross-section to connect to mandrel 60. The ratio of the rotary torque to the axial force is determined solely by the magnetic member pitch. In addition to the primary load, linear bearing 90 is also subjected to secondary loads. A secondary load is a load which does not arise from the fundamental force generation process but rather from inaccuracies in manufacture or assembly, or as a result of intentional misalignment, or system components. A main secondary load experienced by the linear bearings is the magnetic side pull between the mating magnet members of the magnetic coupling. Again, in this embodiment the linear and anti-rotation bearings are designed to allow second magnet member 32 only translating motion to reciprocate within the interventricle chamber of TAH 10 to alternately apply pressure to push plates 21' & 23' (FIGS. 2a & 2b).

Continuing with a center out description, a thin pressure vessel wall 70, best shown in the enlargement to FIG. 6, isolates the inner and outer assemblies of actuator 50. Both magnet members 30 & 32 are designed to be spaced from wall 70 so as not to degrade its structural integrity. As noted, wall 70 allows the outer assemblies to be isolated from the inner assemblies such that only the inner assembly need be exposed to the interventricular environment of the TAH. This allows lubrication to be added to the outer assemblies, including the first magnet member 30, rotary radial and thrust bearing 80 and rotary drive motor 100, notwithstanding that wall 70 might only be 5–10 mils. thick.

Rotating magnet member 30 and back iron 34, along with rotary motor 100, are supported by radial bearings 80. Radial bearings 80 also serve to absorb the axial thrust load on rotating member 30. The primary load on the bearing is the axial thrust, and a key requirement for the radial bearing is to carry this load for the required actuator life, and with the required level of actuator reliability. The selection of the radial bearing is based on a trade-off between bearing life and reliability, and the volume of space available for the motor. Reducing the bearing size reduces the bearing reliability for a given life, but increases the motor volume and eases the motor selection task.

To restate, the present invention broadly comprises a rotary torque-to-axial force (or axial force-to-rotary torque) energy conversion apparatus, with one significant application thereof comprising an actuator for a total artificial heart (TAH) or for a ventricle assist device (VAD). An actuator in accordance with this invention employs a magnetic coupling which totally eliminates contact, wear and friction between the principal moving elements of the actuator. The magnetic coupling, which consists of a helically wound pair of radially polarized magnets of opposite polarity, takes place through a thin isolation wall, permitting important bearing components and their lubricants to be sealed. These components, along with the drive motor, are therefore also isolated from the humid inter-pump space. The new actuator is expected to provide much longer life, lower heat generation, and increased reliability, compared to existing systems. Combined with a new electric motor which takes advantage of the latest magnet materials and design technology, the actuator will be more compact than present electromechanical actuators, providing an improved anatomical fit.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

I claim:

1. A total artificial heart (TAH) comprising:
    a housing having a first ventricle and a second ventricle;
    a first diaphragm coupled to the first ventricle for pumping blood therefrom when actuated towards said housing, and a second diaphragm coupled to the second ventricle for pumping blood therefrom when actuated towards said housing; and
    an actuator for actuating at least one diaphragm of said first diaphragm and said second diaphragm, said actuator comprising
        a rotatable member and a translatable member,
        drive means for imparting rotary torque to the rotatable member, and
        a magnetic coupling associated with the rotatable member and the translatable member for converting rotary torque of the rotatable member to an axial force on the translatable member, said axial force on the translatable member being employed to actuate said at least one diaphragm of said first diaphragm and said second diaphragm, said translatable member reciprocating between said first diaphragm and said second diaphragm and said magnetic coupling comprising a first permanent magnet comprising part of said rotatable member and a second permanent magnet comprising part of said translatable member.

2. The TAH of claim 1, wherein said first permanent magnet comprises interleaved, helical magnet sections of alternating polarities comprising part of said rotatable member, and said second permanent magnet comprises interleaved, helical magnet sections of alternating polarities comprising part of said translatable member.

3. The TAH of claim 2, wherein said actuator alternately actuates said first diaphragm and said second diaphragm, and wherein said actuator includes a plunger affixed to said translating member, said plunger including a first opening for accommodating a first guide pin coupled to said first diaphragm and a second opening for accommodating a second guide pin coupled to said second diaphragm, wherein said first guide pin coupled to said first diaphragm and second guide pin coupled to said second diaphragm are each free to float within said plunger when not forced by said actuator against said first ventricle or said second ventricle, respectively, so that as said actuator pumps blood said first ventricle and said second ventricle are alternately allowed to fill without influence of said actuator.

4. The TAH of claim 2, wherein said interleaved, helical magnet sections of alternating polarities of said first permanent magnet comprise a spirally wound pair of radially polarized permanent magnets of opposite polarity, and wherein said interleaved, helical magnet sections of alternating polarities of said second permanent magnet comprise a spirally wound pair of radially polarized permanent magnets of opposite polarity.

5. The TAH of claim 1, wherein said translatable member resides at least partially within said rotatable member, and said actuator includes anti-rotation apparatus for preventing rotation of said translatable member while allowing axial movement thereof for reciprocation of said translatable member between said first diaphragm and said second diaphragm, wherein rotary torque of said first permanent member is converted to axial movement of said second permanent magnet and hence said translatable member.

6. The TAH of claim 1, wherein said rotatable member and said translatable member are each cylindrical shaped and said translatable member resides at least partially within said rotatable member, said rotatable member and said translatable member being separated by an isolation wall, neither said rotatable member nor said translatable member contacting said isolation wall, said isolation wall allowing lubrication of only one of said rotatable member and said translatable member.

* * * * *

UNITED STATES PATENT AND TRADEMARK OFFICE
CERTIFICATE OF CORRECTION

PATENT NO. : 5,984,960
DATED : November 16, 1999
INVENTOR(S) : Nicholas Gerard Vitale It is certified that error appears in the above-identified patent and that said Letters Patent is hereby corrected as shown below:

Col. 4, between lines 7 and 8, insert --FIG. 3b is a partial enlarged view of the magnet members of FIG. 3a as shown;--.

Col. 4, between lines 13 and 14, insert --FIG. 4b is a partial enlaged view of the magnet members of FIG. 4a as shown;--.

Col. 4, line 19, delete "and".

Col. 4, line 21, delete "6a-6a." and replace with --6a-6a; and--.

Col. 4, between lines 21 and 22, insert --FIG. 6b is a partial enlarged view of the rotary torque-to-axial force energy conversion actuator of FIG. 6 as shown.--.

Col. 4, line 34, delete "FIGS. 3 & 3a" and replace with --FIGS. 3, 3a & 3b--.

Col. 5, line 14, delete "FIGS. 4 & 4a" and replace with --FIGS. 4, 4a & 4b--.

Col. 6, line 8, delete "FIGS. 5, 6 & 6a" and replace with --FIGS. 5, 6, 6a & 6b--.

Signed and Sealed this

Eighteenth Day of July, 2000

*Attest:*

Q. TODD DICKINSON

*Attesting Officer*    *Director of Patents and Trademarks*